United States Patent
Qiu et al.

(10) Patent No.: US 9,529,112 B2
(45) Date of Patent: Dec. 27, 2016

(54) RESISTIVITY OF CHEMICALLY STIMULATED RESERVOIRS

(71) Applicant: SCHLUMBERGER TECHNOLOGY CORPORATION, Sugar Land, TX (US)

(72) Inventors: Xiangdong Qiu, Al-Khobar (SA); Stephen John Remane Dyer, Al-Khobar (SA); Reza Taherian, Al-Khobar (SA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 75 days.

(21) Appl. No.: 14/251,419

(22) Filed: Apr. 11, 2014

(65) Prior Publication Data

US 2015/0293255 A1    Oct. 15, 2015

(51) Int. Cl.
*G01V 3/28* (2006.01)
*G01N 33/24* (2006.01)

(52) U.S. Cl.
CPC ............. *G01V 3/28* (2013.01); *G01N 33/24* (2013.01)

(58) Field of Classification Search
None
See application file for complete search history.

(56) References Cited

U.S. PATENT DOCUMENTS 3,136,942 A * 6/1964 Schuster ............... G01V 3/24
                                                      324/374
6,600,321 B2 * 7/2003 Evans ................ E21B 47/0002
                                                      175/50

(Continued)

FOREIGN PATENT DOCUMENTS

WO    2013089897 A2    6/2013

OTHER PUBLICATIONS

Montaron et al., "SPE 111147: Shapes of Flood Fronts in Heterogeneous Reservoirs and Oil Recovery Strategies," SPE International, 2007: pp. 1-18.

(Continued)

*Primary Examiner* — Jermele M Hollington
*Assistant Examiner* — Suresh K Rajaputra
(74) *Attorney, Agent, or Firm* — Bridget Laffey

(57) ABSTRACT

A chemical stimulation system and a resistivity tool are disposed in a wellbore. Chemical stimulation operations are performed in the wellbore using the chemical stimulation system. Resistivity measurements are made with the resistivity tool before, during, and/or after the chemical stimulation operations. The resistivity measurements may be used to determine the porosity of a formation penetrated by the wellbore. A wormhole distribution and/or penetration in the formation is determined based on the resistivity measurements. Decisions regarding stimulation operations are made based on the determined wormhole distribution and/or penetration. The resistivity tool may be modular and have various arrays allowing various depths of investigation. The depths of penetration of the wormholes into the formation may be determined using the measurements from the multiple depths of investigation. The volume of the formation that is dissolved by the chemical stimulation operations may also be estimated.

22 Claims, 11 Drawing Sheets

(56) References Cited

U.S. PATENT DOCUMENTS

| | | | | |
|---|---|---|---|---|
| 6,668,922 | B2* | 12/2003 | Ziauddin | A61L 2/20 166/250.02 |
| 6,691,805 | B2* | 2/2004 | Thaemlitz | C09K 8/32 166/254.2 |
| 6,714,014 | B2* | 3/2004 | Evans | E21B 47/024 324/355 |
| 7,112,557 | B2* | 9/2006 | Thaemlitz | C09K 8/32 507/103 |
| 7,382,136 | B2* | 6/2008 | Hayman | E21B 47/011 324/367 |
| 7,617,873 | B2 | 11/2009 | Lovell et al. | |
| 7,819,181 | B2 | 10/2010 | Entov et al. | |
| 7,909,096 | B2* | 3/2011 | Clark | E21B 33/124 166/250.17 |
| 7,942,202 | B2 | 5/2011 | Poitzsch et al. | |
| 8,191,416 | B2* | 6/2012 | Kuchuk | E21B 49/008 73/152.41 |
| 8,629,678 | B2* | 1/2014 | Gold | G01V 3/20 324/367 |
| 2003/0205083 | A1 | 11/2003 | Tubel et al. | |
| 2004/0100263 | A1 | 5/2004 | Fanini et al. | |
| 2004/0104029 | A1 | 6/2004 | Martin | |
| 2006/0184346 | A1* | 8/2006 | Panga | E21B 43/16 703/9 |
| 2007/0257678 | A1* | 11/2007 | Wang | G01V 3/20 324/366 |
| 2011/0067882 | A1 | 3/2011 | Yeriazarian et al. | |
| 2014/0212006 | A1* | 7/2014 | Zhao | G06T 7/0004 382/109 |
| 2015/0041123 | A1* | 2/2015 | Troshko | E21B 43/255 166/254.1 |

OTHER PUBLICATIONS

Yale et al., "SPE 134313: Large-Scale Laboratory Testing of Petroleum Reservoir Processes," SPE International, 2010: pp. 1-14.
International Search Report for corresponding International App No. PCT/US2015/024431, Jul. 13, 2015, 5 pages.
PCT/US2015/024431, Written Opinion for corresponding International App No. PCT/US2015/024431, Jul. 13, 2015, 8 pages.

* cited by examiner

RESISTIVITY OF CHEMICALLY STIMULATED RESERVOIRS

BACKGROUND

In the petroleum industry, chemical treatment of a downhole formation is an established technique to improve the rate and amount of oil production. For example, hydrofluoric acid (HF) may be used in sandstone rocks to dissolve the rock or other solids, thereby providing a flow path for the formation fluid to flow through and be produced. For carbonate rocks, hydrochloric acid (HCl), organic acids, or a chelating agent such as ethylenediaminetetraacetic acid (EDTA) may be used to dissolve calcite ($CaCO_3$) and serve the same purpose. Calcite reacts readily with HCl and dissolves, leaving behind a channel that acts as a conduit for the formation fluid to flow through and be produced. The high reactivity of $CaCO_3$ to acids has made acidizing a common practice in carbonate reservoirs.

Although acidizing is very common, especially in carbonate formations, the treatment process is monitored in a very limited sense. The most common parameters monitored during a chemical (acid) treatment include injection pressure, injection rate, downhole pressures, and (more recently) distributed temperature, which can be related to the extent of the treatment. However, temperature monitoring, for example, is not particularly effectual, and if there is poor zonal coverage of chemical treatment, such poor zonal coverage may not be discovered until later, in the production phase, when a low production rate is experienced. It is important to be able to assess treatment efficiency during treatment operations to avoid poor zonal coverage, and to optimize the efficiency of the chemicals injected based on the formation properties encountered at that injection site.

The electrical resistivity of a formation is an important parameter in determining hydrocarbon and water saturation. Electricity can pass through a formation due to the conductivity of formation water. Dry rock is generally a very poor electrical conductor. Therefore, subsurface formations have measurable resistivities because of water (or injected fluids) in the porous media. The resistivity of a formation depends, at least in part, on: (1) the resistivity of the formation fluid; (2) the amount (or saturation) of water present; and (3) the pore structure geometry (e.g., pore shape and connectivity, wormhole, fracture). Formation resistivity is measured by sending a current into the formation and measuring the resulting voltage drop. The ratio of voltage to current equals the formation resistivity. In the field of well logging, the current may be directly injected into the formation or eddy currents may be induced in the formation by a varying magnetic field.

SUMMARY

A chemical stimulation system and a resistivity tool are disposed in a wellbore. Chemical stimulation operations are performed in the wellbore using the chemical stimulation system. Resistivity measurements are made with the resistivity tool before, during, and/or after the chemical stimulation operations. The resistivity measurements may be used to determine the porosity of a formation penetrated by the wellbore. A wormhole distribution and/or penetration in the formation is determined based on the resistivity measurements. Decisions regarding stimulation operations are made based on the determined wormhole distribution and/or penetration. The resistivity tool may be modular and have various arrays allowing various depths of investigation. The depths of penetration of the wormholes into the formation may be determined using the measurements from the multiple depths of investigation. The volume of the formation that is dissolved by the chemical stimulation operations may also be estimated.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. Embodiments of determining are described with reference to the following figures. The same numbers are generally used throughout the figures to reference like features and components.

DETAILED DESCRIPTION

Figure 1:
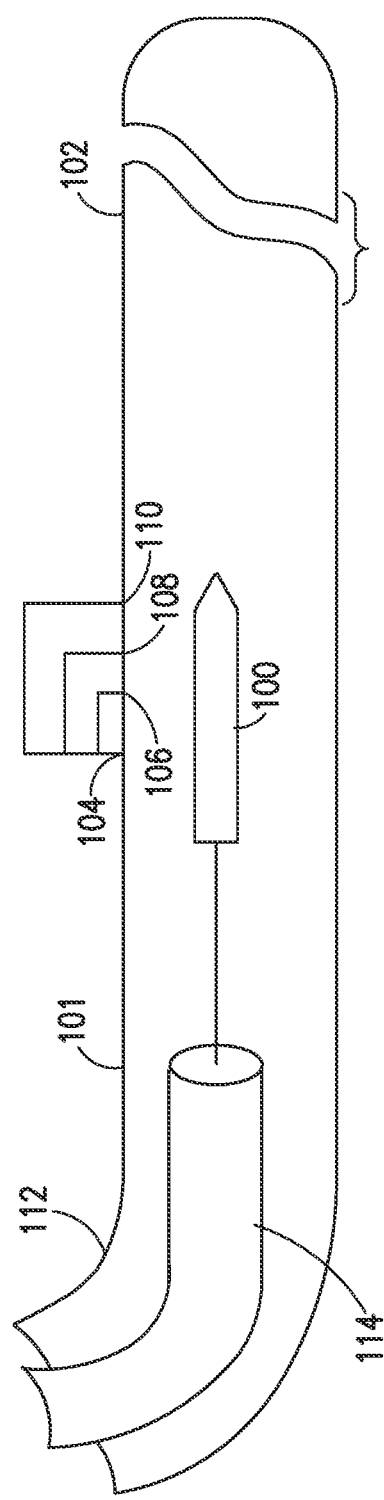
FIG. 1 is a schematic drawing showing an embodiment of a conveyance mechanism and a resistivity tool in a wellbore, in accordance with the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Some embodiments will now be described with reference to the figures. Like elements in the various figures may be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used here, the terms "above" and "below," "up" and "down," "upper" and "lower," "upwardly" and "downwardly," and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship, as appropriate. It will also be understood that, although the terms first, second, etc. may be used herein to describe various elements, these elements should not be limited by these terms. These terms are used to distinguish one element from another.

The terminology used in the description herein is for the purpose of describing particular embodiments and is not intended to be limiting. As used in the description and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

A system and method to monitor the resistivity of a chemically stimulated well is disclosed. The resistivity information can be used to infer zonal coverage, for example, and contributes to maximizing the value of a chemical treatment. During treatment (e.g., acidization) dissolution channels (i.e., wormholes) develop as acid propagates into a formation. Resistivity measurements and quantitative analysis of the propagation of the dissolution front and wormhole development can assist an operator in performing the stimulation treatment. The resistivity profiles may be functionally related to various quantities such as, but not limited to, wormhole propagation profiles, acid flow profiles, and reaction product flow profiles.

As stated above, chemical stimulation of an oil reservoir by injecting chemicals into the rock can improve the flow of formation fluids. Although the chemicals used are primarily acids, other chemicals such as chelating agents may also be used. While embodiments described in detail below are for cases in which the fluid is an acid, they are equally applicable for other chemical agents.

A resistivity measuring device may be used in conjunction with the well (chemical) stimulation system (conveyed using a coiled tubing, for example), and may be used to monitor the formation resistivity. Resistivity data may be acquired at three stages of a well stimulation treatment: pre-job, during the job, and post-job. Changes in the measured resistivity are interpreted to estimate the increased porosity that accompanies the matrix acidization. Resistivity measurements with progressively deeper depths of investigation (DOI) may be used to map the extent of wormholes formed as a result of the acid treatment. The volume of the formation that is dissolved and the radial extent of the wormhole may be estimated. The resistivity tool may have an azimuthal resistivity array that will allow wormhole propagation direction as well as depth of penetration to be determined, further improving the treatment understanding.

When acid is injected into a formation, it reacts with the solid material at the pore wall ($CaCO_3$ for carbonate formations, for example) and dissolves part of that material. This causes the average pore diameter, and correspondingly, the total porosity to increase. The increased average pore diameter leads to higher permeability, which is the reason to perform this operation. The chemical reaction between hydrochloric acid and calcite is given by:

$$2H^+ + 2Cl^- + CaCO_3 \leftarrow\rightarrow Ca^{++} + CO_2 + 2Cl^- + H_2O \qquad (1)$$

Equation 1 shows that as the acid reacts, its active component (H+) is consumed and the acid becomes spent. The ratio of spent acid to active acid is a dynamic quantity which tends toward more spent acid as the treatment progresses. As a result, the concentrations of different ionic species, which control the resistivity, vary as a function of radial distance, and merit being considered in detail. In addition, the resistivity is measured as a function of time. As the reaction between the acid and calcite progresses, the resistivity of the formation changes, thereby reflecting the amount of acid that is spent. For reference, the formation resistivity is measured before pumping acid into the formation. Measurements are also performed during and after the acidizing operation. Those measurements can be used to obtain useful information on the radial extent and the volume of wormholes.

FIG. 1 shows a horizontal well 112 undergoing chemical stimulation. The length of the well between points 101 and 102 (i.e., the treatment zone) is treated with acid. This length is on the order of 100 s to 1000 s of feet long. Also shown is a coil tubing 114 that extends from the treatment zone to the surface and is used to convey acid being pumped into well 112. A resistivity tool 100 is disposed in the treatment zone and is used to measure the formation resistivity as a function of time and depth into the formation. The tool 100 has multiple depths of investigation (though it need not). For the particular case of a tool with three DOIs, FIG. 1 shows rectangular shapes within which the formation is being sampled for each DOI. The rectangle between 104 and 106 is the shallowest DOI. The rectangle between 104 and 108 is of intermediate depth, and that between 104 and 110 is the deepest DOI. While three DOIs are shown for this particular example, tool 100 may have more or fewer DOIs. The sensitive region of tool 100 for each DOI is generally not of rectangular shape, but here it is approximated as such. More accurate shapes for the sensitive region may be used in the data analysis, if desired. The region of sensitivity of a resistivity tool is generally between a transmitter antenna and a receiver antenna, or between the transmitter antenna and each of multiple receiver antennas for a multi-array tool. In the embodiment shown, a single transmitter and three receivers are assumed so that the rectangles coincide on one edge above the transmitter antenna at 104. Also, the sensitive region is drawn on one side of the well, but in most cases it extends circumferentially around the borehole, though side-looking resistivity tools are available.

Various resistivity tools having multiple depths of investigations are commercially available and suitable for use. Those tools have multiple arrays, each array providing a different DOI. The depth of investigation of an array in a resistivity tool is generally proportional to the distance between the transmitter antenna, T, and the receiver antenna, R, in that array. It is common in the art to use one transmitter antenna and multiple receivers that are spaced from the transmitter at progressively longer distances. With this design a tool is made with as many arrays as the number of receiver antennas. The maximum DOI of those tools is generally on the order of six feet, in part depending on the conductivity of the formation. This maximum DOI (distance between T and R) is also limited in part because of transportation issues; a very long tool cannot be easily transported. The length available in a logging truck limits the maximum length of the logging tools. Resistivity measurements from such tools are more than adequate if wormholes do not extend radially beyond the maximum DOI limit. However, if the wormholes extend beyond the maximum DOI of those tools, one will not be able to properly monitor the deeper front using these tools. For deeper DOIs, a modular tool may be used instead.

Figure 2:
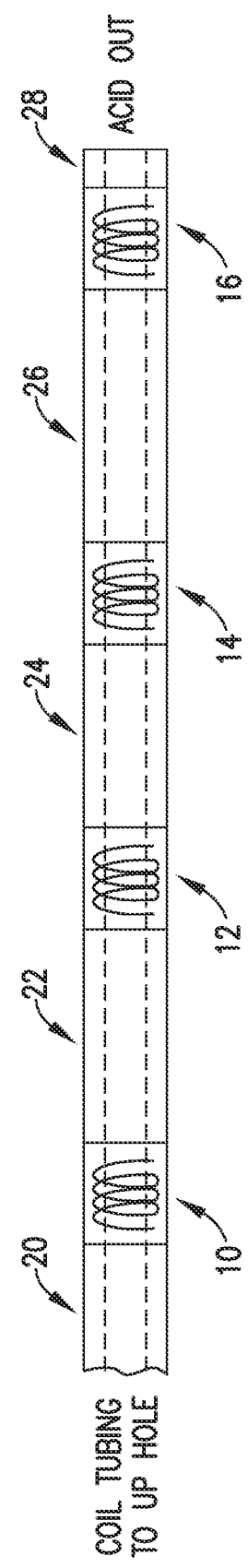
FIG. 2 is a schematic drawing showing a modular resistivity tool, in accordance with the present disclosure.

To have longer depths of investigation, it is possible to make the tool using multiple modules that are small enough to be transportable. When these modules are connected together, it is possible to have T-R distances larger than what is possible with a single tool. An example modular resistivity tool is shown in FIG. 2. The tool is made up of multiple units of antennas (10, 12, 14, and 16) and spacers (22, 24, 26, and 28) and is attached to the end of a coil tubing conveyance mechanism 20. Each of these units can be an independent module. In some embodiments, more than one of these antennas or spacers can be combined into one module. With this design, longer T-R spacings and thereby longer DOIs are achieved. Further flexibility afforded by the modular approach is the freedom of being able to use a desired number of antennas to create a desired number of arrays. The length of the spacers can be changed to make arrays with virtually any desired DOI. This is contrary to normal tools wherein both the number of antennas and the spacing between the antennas is fixed. Yet another measure of flexibility of the modular design is being able to use spacers that may serve an alternative specific purpose and are more than just passive spacers. For example, one of the spacers may be used as an outlet for the acid, while another may carry instruments to make measurements such as the local temperature. The modules may have inner passageways to allow fluid, such as chemical stimulation fluid, to pass through their interiors.

During the acidization operation, acid is injected into the borehole at high pressure and it moves into the rock formation while reacting with the pore surface. Since the movement of the acid is not instantaneous, the resistivity signals from different DOIs will measure different time-dependent signals. The time dependence and the difference between signals with different DOIs contain information about the length and width of the wormholes. The total signal from each DOI is proportional to the cumulative area of the wormholes carved in the sensitive zone.

The measured resistivity data can be qualitatively interpreted as showing the density of the wormholes, their maximum depths, and the time it takes to completely consume the injected acid. However, more quantitative interpretation is also possible. This can be done, for example, by collecting the governing equations and solving those equations simultaneously. Below we describe an analytical approach to interpret the data. This approach provides a physical understanding of how the system works. Certain approximations made along the way can be avoided if a software package is developed and used for data analysis. Thus, numerical techniques may be used for more accurate and quantitative information on the wormholes.

In the field of resistivity logging, the measured resistivity is used to derive petrophysical properties such as porosity and saturation using Archie's relation:

$$\frac{R_o}{R_w} = \frac{1}{\Phi^m S_w^n} \quad (2)$$

Ro is the formation resistivity, Rw is the resistivity of water in the pores, $\Phi$ is the porosity, Sw is the water saturation, and m and n are the Archie exponents. Archie's relation is applicable for chemical treatment operations, but the interpretation is more complicated compared to resistivity logging. Before any chemical treatment, a resistivity log is preferably recorded and used to determine Rw (it is considered known in most cases), porosity, saturation, m, and n.

The acid reaction affects the formation conductivity in the following ways. When acid is injected into the rock, it changes Rw (see Eq. 1), so it is preferable to determine Rw prior to or at the onset of the analysis. When hydrocarbons are present in the pore space, Sw is less than unity and its true value is preferably included in the analysis. When the acid solution is injected into the formation, it sweeps (replaces) some of the connate water and the hydrocarbon fluids. Because the acid is soluble in water but not in hydrocarbons, to a good approximation one may assume some of the connate water remains in place and mixes with the acid while the hydrocarbons are completely swept out of the pore space.

At the start of an acidizing operation, one normally performs a "pre-flush" with water to: (1) clean out any oil traces from the pore space (and therefore effectively saturate the pores with water); and (2) test the injectability of the formation. If a water pre-flush is performed, one may assume Sw1, the water saturation at t=0, equals 1. Also, although the acid starts reacting immediately upon contact with the pore volume surface, at time t=0 we assume the effect of the acid reaction is negligibly small. As a result, the instantaneous fluid conductivity is a function of the volume fraction and resistivity of the acid ($V_a$ and $R_a$) and the volume fraction and resistivity of the un-swept original water ($R_c$ and $V_c$). To determine a sweep efficiency, note that at t=0 the parameters in Equation 2 that change are the connate water resistivity (from $R_w$ to $R_{w1}$), the water saturation (from Sw to Sw1=1), and the rock resistivity ($R_o$ to $R_{o1}$). Taking a ratio of Equation 2 before and immediately after acid injection yields:

$$R_{w1} = \frac{R_{o1}}{R_o} \frac{R_w}{S_w^n} \qquad (2.5)$$

The parameters on the right-hand side are known, so $R_{w1}$ can be computed. The calculated $R_{w1}$ is also related to the resistivity of its two constituents:

$$R_{w1} = V_c R_c + V_a R_a \qquad (2.75)$$

or, $$R_{w1} = (1-b)R_c + b(R_a) \qquad (3)$$

where b=Va is the pore volume fraction occupied by injected acid. The resistivity measurement provides $R_{w1}$ and since the other two resistivities in Equation 3 are known, b can be calculated.

Now looking at $R_w$ at times t>0, $R_w$ does not remain constant. The acid reacts with the carbonate matrix causing the conductivity of the fluid to change according to the chemical reaction shown in Equation 1. Note that calcium carbonate, water, and $CO_2$ are not conductive and do not, at least not directly, contribute to Rw. The contribution of the water generated in Equation 1 is to cause dilution. The HCl solution used for acidization is typically 26% HCl and 74% water. Converting this to a ratio of moles:

$$\frac{26}{36.354} * \frac{18}{74} = 0.17 \qquad (3.5)$$

HCl constitutes 17% of the number of moles while water has an 83% share. The ratio of HCl to water is further reduced when the un-swept water is also added. As a result, the dilution effect of water produced from Equation 1 is negligible.

The produced $CO_2$ from Equation 1, if it is in gas phase, can have a strong perturbing effect on the conductivity. However, the typical pressures and temperatures of acidization operations are generally above the supercritical conditions of $CO_2$, causing the gas to be converted to a supercritical liquid, in which case its volume is very small and can be ignored. The effect of $CaCO_3$ will be discussed below. To a first approximation and for the sake of clarity, we ignore the combined effect of water and $CO_2$ here, but such effect may be included if one so chooses.

The result of the reaction shown in Equation 1 is to replace two H+ ions with one Ca++ ion. Although the number of charges remains the same, the number of charge carriers (ions) decreases. In addition, the mobility of H+ is much greater than that of Ca++. The conductivity of a 1 molar HCl solution is 0.282 S/m while that of $CaCl_2$ is 0.016 S/m, even though a mole of $CaCl_2$ contributes two chloride ions. The higher mobility of H+ is the dominant factor controlling the conductivity of the solution. The net result of the Equation 1 reaction on the pore water is to reduce its conductivity. This effect is demonstrated in the simulation results shown in FIG. 3. In these simulations a constant number of moles of HCl are reacted with varying numbers of moles of $CaCO_3$ and the conductivity of the resulting solution is calculated. As the number of moles of calcite increases, more of the acid is spent. More H+ ions are replaced with Ca++ and the conductivity decreases. In the limiting cases when the number of moles of calcite is more than half the number of moles of acid, the solution conductivity remains constant since no reaction takes place.

Figure 3:
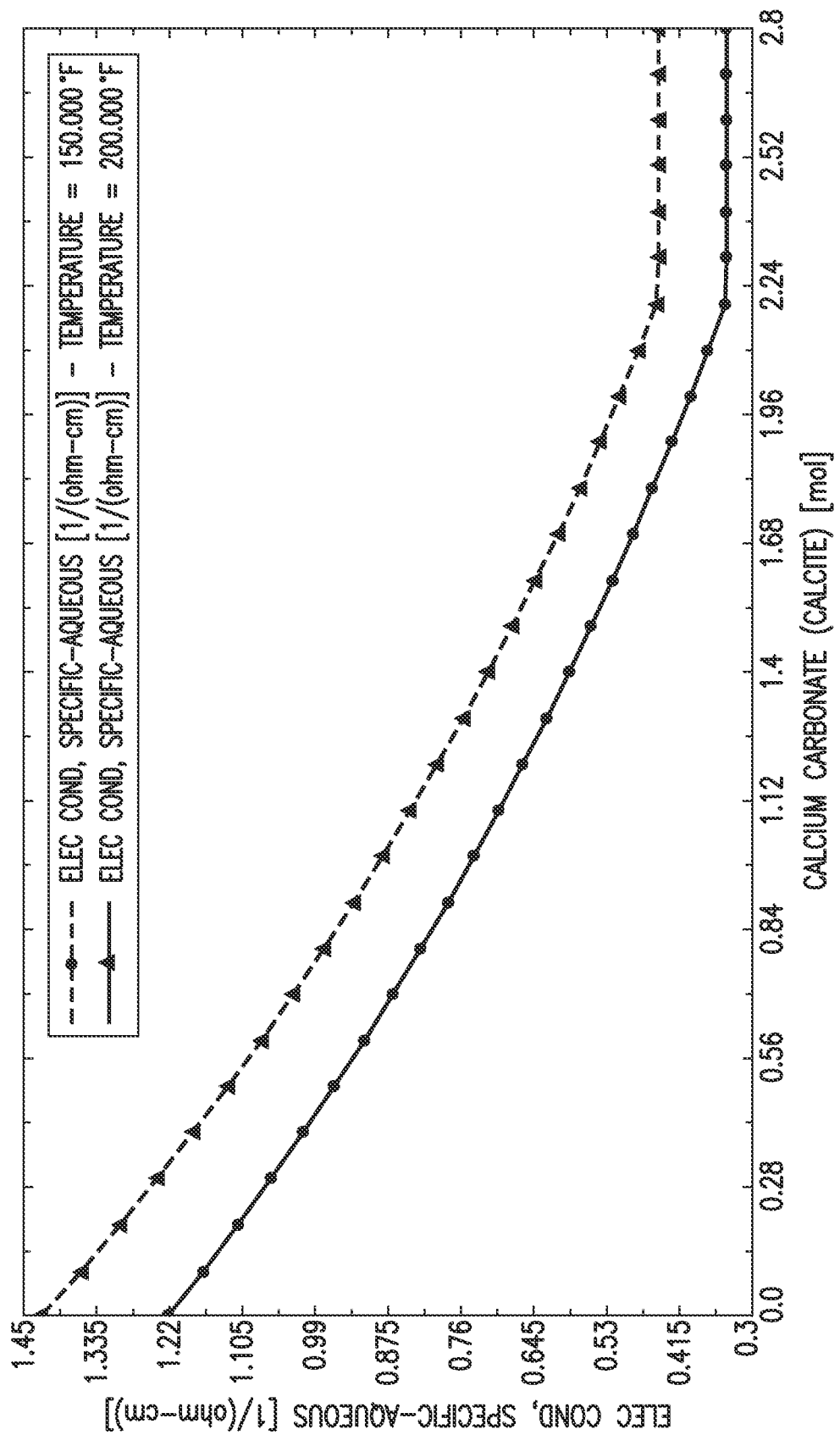
FIG. 3 is a graph showing the electrical conductivities measured during 4.42M of HCl reacted with calcite after injection into the formation at 150° F., 200° F., and 1000 psi, in accordance with the present disclosure.
Figure 4:
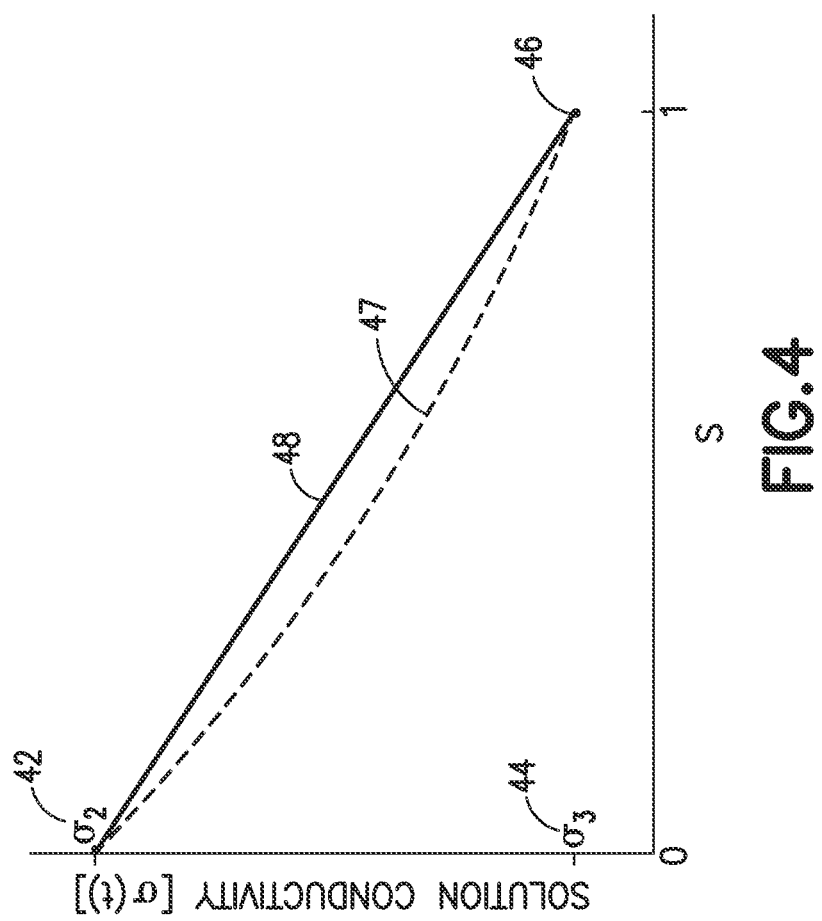
FIG. 4 is a graph showing a solution conductivity versus the spent factor, in accordance with the present disclosure.

In a practical sense, in an acidization operation there is an infinite supply of calcite, and it is only a matter of time when the acid is spent. Thus, FIG. 3 can be re-drawn with the horizontal axis representing time. FIG. 3 can be redrawn with the horizontal axis showing the amount of spent acid. This is shown in FIG. 4. The variable on the horizontal axis is the "spent factor," which equals one when the acid is spent, and zero before the acid starts reacting with the calcite. The vertical axis shows the conductivity of water in the pore spaces. The solution conductivity varies between those two limits in the intermediate stages. When S=0 (point 42) the solution conductivity is equal to (1/Rw1). The solution conductivity at S=1 (point 44) can be easily calculated since the volume of acid, b, and its concentration are already known from Equation 3. The points between these two limits show the progression of acid being reacted, causing the conductivity of the solution to decrease. FIG. 3 shows an almost linear variation between the two (fresh and spent) limits. We show the approximate linear dependence (line 48) in FIG. 4, but the actual variation (dotted curve 47) can be fit to an appropriate function and that function may be used if more accuracy is desired. The time-dependent water conductivity can be related to the number of moles of spent acid at each point in time (or S) using the following relation:

$$\sigma(t) = \sigma_2 - (\sigma_2 - \sigma_3)S(t) \qquad (4)$$

The conductivity obtained from Equation 4 can be easily converted to the corresponding resistivity, Rw(t), by taking its reciprocal.

Figure 5:
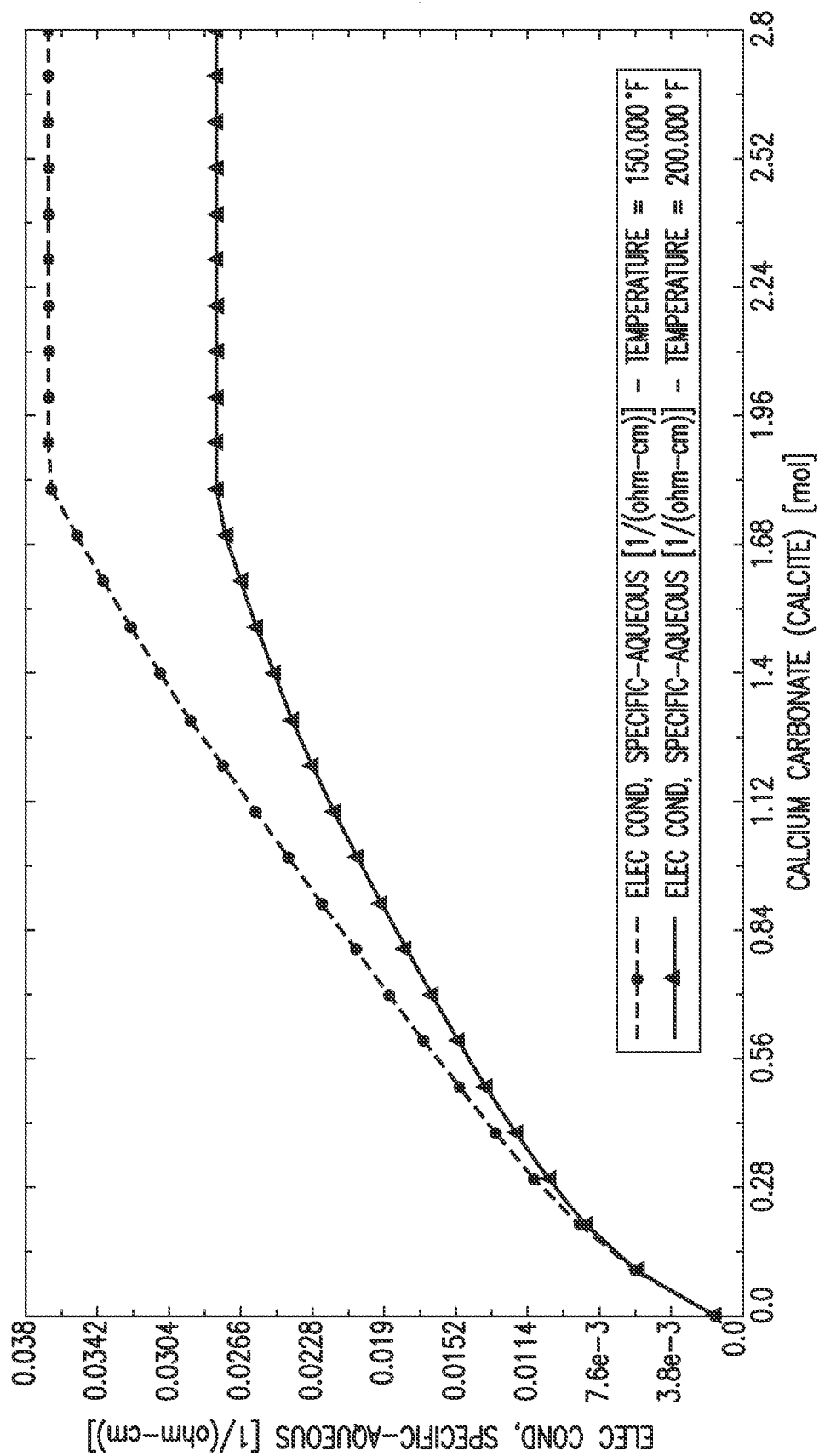
FIG. 5 is a graph showing the electrical conductivities measured during 4.42M of acetic acid reacted with calcite after injection into the formation at 150° F., 200° F., and 1000 psi, in accordance with the present disclosure.
Figure 6:
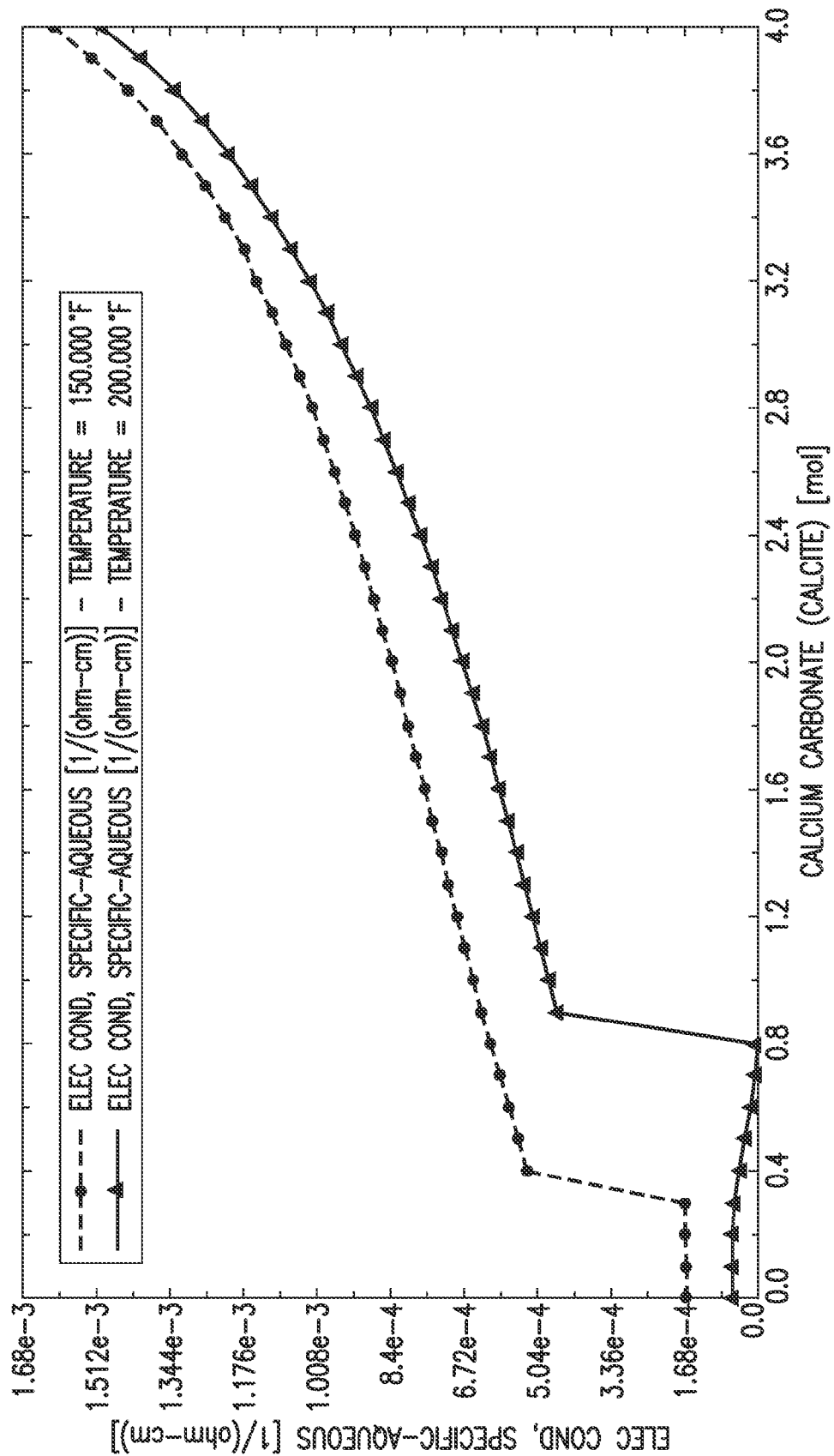
FIG. 6 is a graph showing the electrical conductivities measured during 4.42M of disodium dihydrogen ETDA reacted with calcite after injection into the formation at 150° F., 200° F., and 1000 psi, in accordance with the present disclosure.
Figure 7:
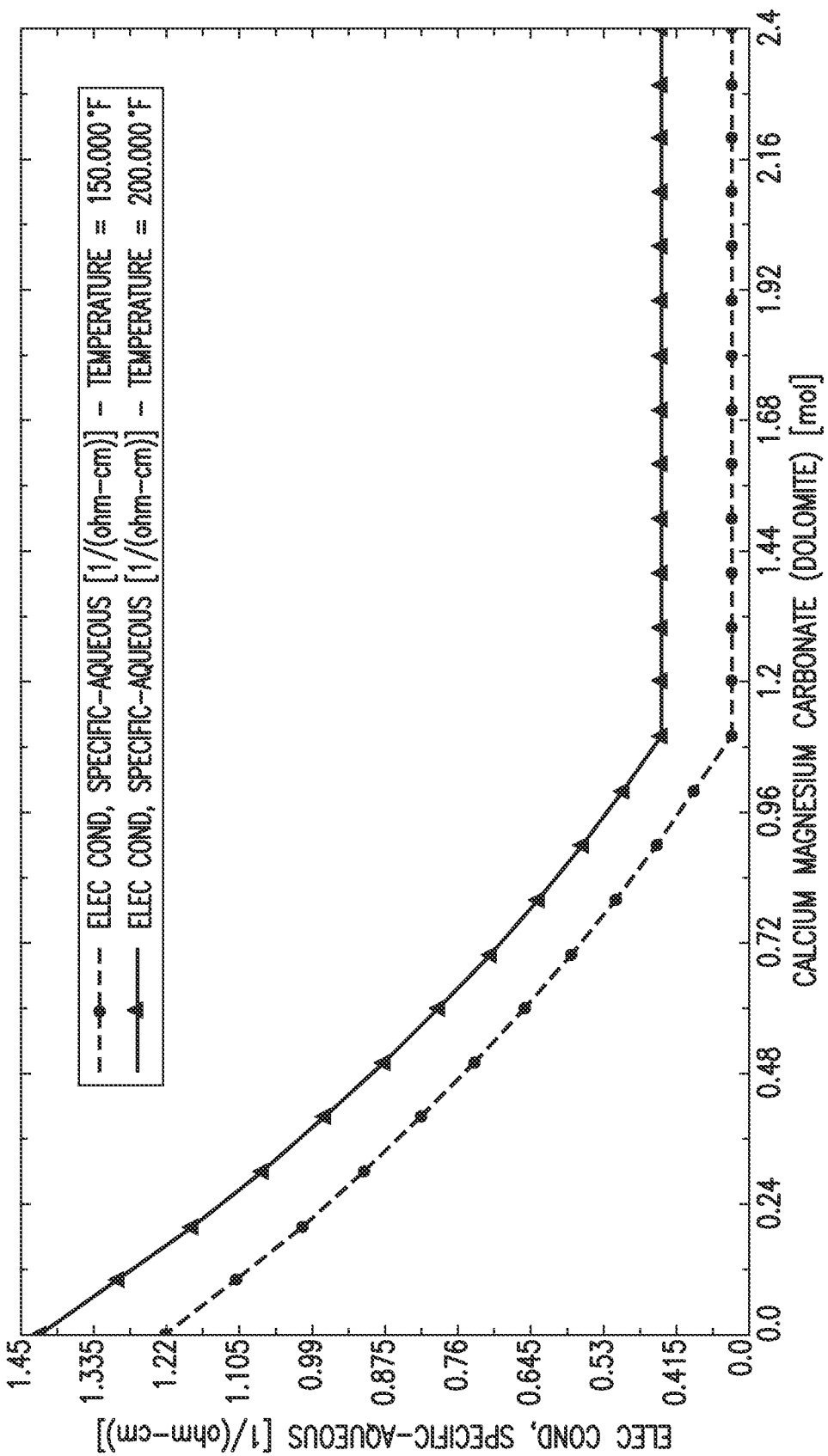
FIG. 7 is a graph showing the electrical conductivities measured during 4.42M of HCl reacted with dolomite after injection into the formation at 150° F., 200° F., and 1000 psi, in accordance with the present disclosure.
Figure 8:
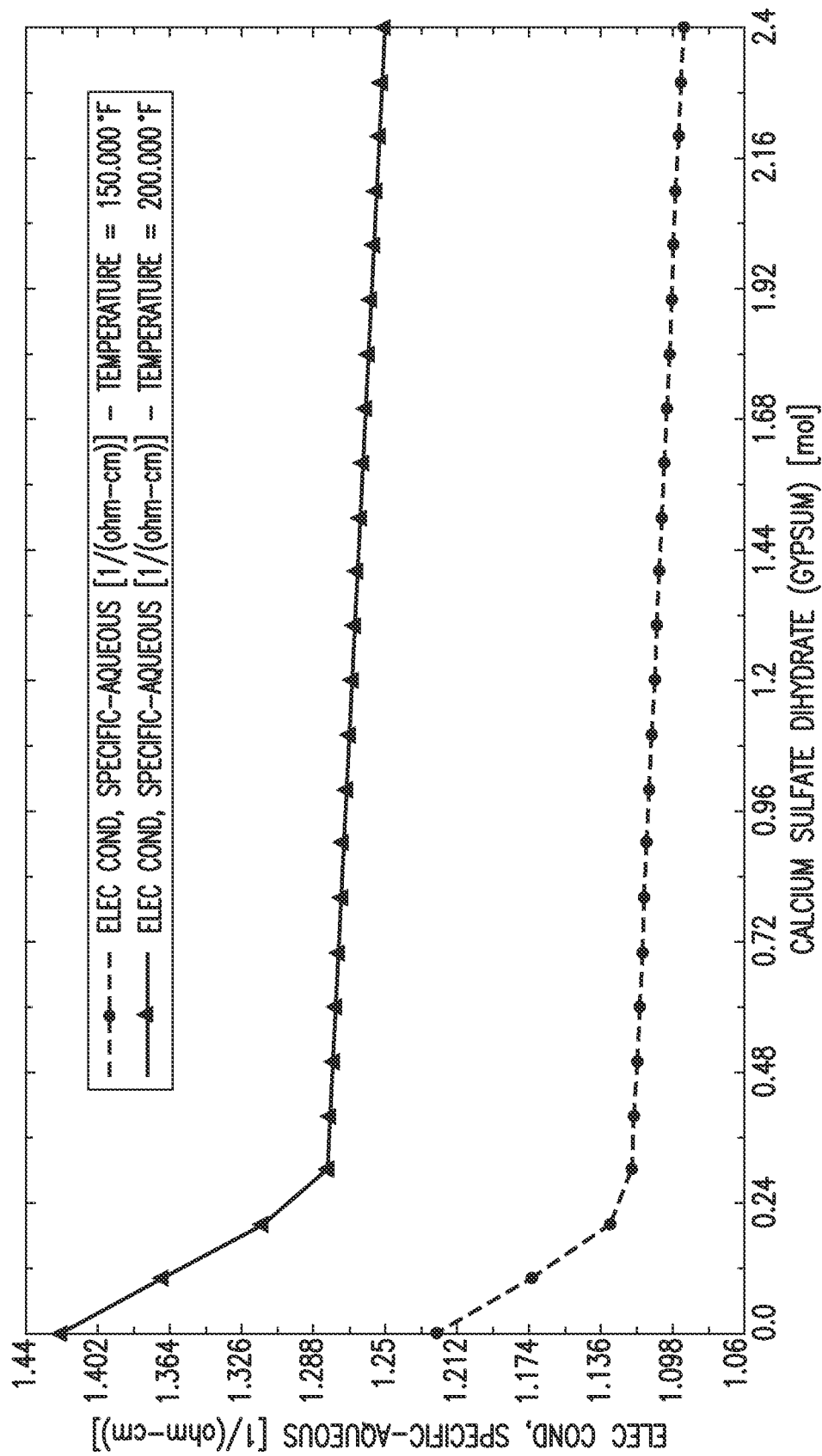
FIG. 8 is a graph showing the electrical conductivities measured during 4.42M of HCl reacted with gypsum after injection into the formation at 150° F., 200° F., and 1000 psi, in accordance with the present disclosure.

The calculations done to generate FIG. 3 are made for HCl reacting with calcite, but the method described herein is not limited to strong acids or calcite based rocks. FIG. 5 shows the same calculations as those leading to FIG. 3 for acetic acid dissolving calcite. In this case the weaker acid starts with low conductivity, but as it reacts it is converted into its corresponding acetate salt and the conductivity of the solution actually increases. This is an opposite trend compared to the HCl and therefore requires a slightly different form for Equation 4. Likewise FIG. 6 is equivalent to FIGS. 3 and 4 except the calculation is done for a chelating agent (EDTA) dissolving calcite. It behaves similarly to acetic acid. FIGS. 7 and 8 show the acidization of dolomite and gypsum formations. Those two figures show the same dependence as when the reacting acid is HCl (strong acid). Any of the FIGS. 5-8 may be re-drawn with S (the spent factor) as the independent variable (like FIG. 4) and the same analysis as above may be applied.

Unlike the situation in resistivity logging, the porosity is not constant during an acidization operation. A by-product of the acid reaction is the dissolution of the rock solid, causing the porosity to increase. From Equation 1, it is evident that two moles of HCl dissolves one mole of calcite. Thus, knowing the number of moles, $M_{HCl}$, of HCl injected into a known volume of the formation, Vt, it is possible to calculate the volume of solid calcite dissolved by it, causing the additional porosity. Here Vt is chosen to be the volume of formation sampled by a particular array of a resistivity tool. Before starting chemical stimulation, the porosity is defined as:

$$(1 - \phi_1) = \frac{V_{s1}}{V_t} \qquad (5)$$

where, as before, V refers to the volume sampled by the resistivity tool and the subscripts s and t refer to the solid phase and total.

The volume of calcite dissolved is:

$$\frac{V_{calcite}(t)}{V_t} = \frac{M_{calcite} * 100}{\rho_{calcite} V_t} == \frac{2M_{HCl}S(t) * 100}{\rho_{calcite}} \qquad (6)$$

where the molecular weight of $CaCO_3$ (100) is included explicitly and the total volume is incorporated into the definition of the number of moles of HCl. As a result the porosity will change from that of Equation 5 by what is predicted from Equation 6:

$$(1 - \phi_2(t)) = \frac{V_{s1} - V_{calcite}(t)}{V_t} = (1 - \phi_1) - \frac{2M_{HCl}S(t) * 100}{\rho_{calcite}} \qquad (6.5)$$

or $$\phi_2(t) = \phi_1 + \frac{2M_{HCl}S(t) * 100}{\rho_{calcite}} \qquad (7)$$

This causes the void volume to increase from Φ1 to Φ2, which in turn increases the formation resistivity, as can be seen from the inverse dependence of Equation 2 on the porosity. Archie's relation can now be expressed as:

$$R_{o2}(t) = R_{w2} \frac{1}{\phi_2^m(t)} = \left[\frac{1}{\sigma_2 - (\sigma_2 - \sigma_3)S(t)}\right] \frac{1}{\phi_2^m(t)} \qquad (8)$$

Here we have assumed m is constant. This is an acceptable assumption since this parameter has a relatively small dynamic range. Looking at the form of Equation 8, it is easier to write it in reciprocal form and work in the conductivity domain:

$$\sigma_{o2}(t) = \frac{1}{R_{o2}} = [\sigma_2 - (\sigma_2 - \sigma_3)S(t)][\phi_2^m(t)] \qquad (9)$$

Equation 9 has two variables, Φ2 and S, that are interrelated through Equation 7. The combination of Equations 7 and 9 can be solved to obtain both the new porosity Φ2 and the spent index S. Another approach is to solve Equation 7 for S and substituting in Equation 9, which leads to the following relation:

$$\phi_2^m(t) = \frac{\sigma_2}{\sigma_{o3}} - \frac{(\sigma_2 - \sigma_3)\rho_{calcite}}{2M_{HCl} * 100}(\phi_2(t) - \phi_1) \qquad (10)$$

This equation has porosity on both sides and may be solved at least by varying porosity iteratively until the two sides of Equation 10 become equal. This technique is well known in the field of numerical methods. A similar relation for S(t) can be derived which can also be solved iteratively, but one may substitute the determined porosity from Equation 10 into either Equation 7 or Equation 9 and solve for S. For this purpose, the following form of Equation 7 can be used without the need for iteration:

$$S(t) = \frac{\sigma_{o2}(t)\phi_2^{-m}(t) - \sigma_2}{\sigma_3 - \sigma_2} \qquad (11)$$

Thus, using a resistivity tool we can measure the formation conductivity at various points of time during an acidization operation and use Equation 10 to solve for Φ2, followed by using either Equation 7, 9, or 11 to solve for S.

In the limit, when the acid is spent, S=1 and Equation 9 takes a simpler form:

$$\sigma_{o3} = [\sigma_2 - (\sigma_1 - \sigma_3)][\phi_3^m(t)] \qquad (11.5)$$

$$\phi_3 = \left(\frac{\sigma_3}{\sigma_{o3}}\right)^{-m} \qquad (12)$$

Equation 12 can be used to determine Φ3, which we relate to the wormhole porosity.

The porosity Φ3 is not the porosity of individual wormholes. Rather it is the new effective porosity of the rock mass in the volume of investigation of the resistivity tool. It includes porosities whether part of the wormhole or not. The resistivity measurement provides the porosity increase from Φ1 to Φ3 in its sensitive region. At the end of the acidizing operation, the sensitive region is composed of a number of wormholes that have a total volume of Vh2 or Vh3 (if S=1) and the remaining rock mass that has not been dissolved by the acid injection.

Figure 9A:
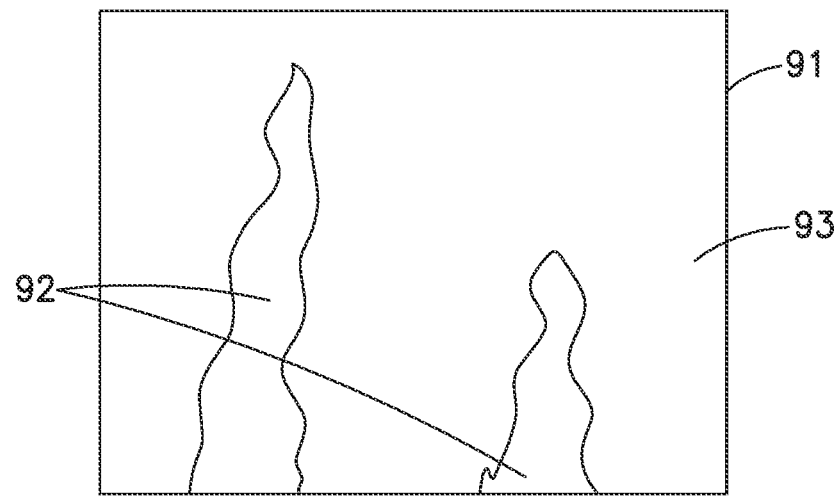
FIG. 9A is a schematic drawing showing two dissolution channels (wormholes) penetrating a rock matrix, in accordance with the present disclosure.
Figure 9B:
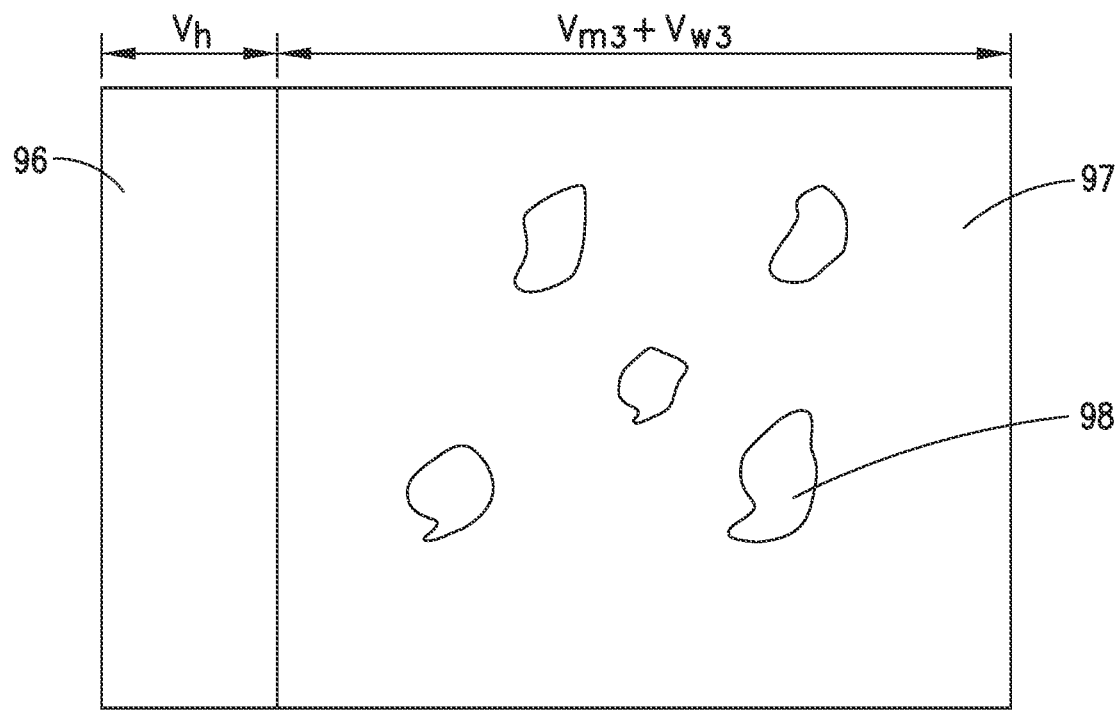
FIG. 9B is a schematic block drawing reflecting the volumes of the wormholes, the solid rock matrix, and the pores within the rock matrix for the sensitivity region identified in FIG. 9A, in accordance with the present disclosure.

FIG. 9A shows the sensitive region 91 of a downhole resistivity tool with two wormholes 92 having volume Vh (figure element 96 in FIG. 9B). FIG. 9A further shows a portion of the original rock matrix 93 that has not been affected by the acidization operation. It has volume Vt–Vh (since Vt represents the entire volume). The unaffected part of the rock is porous with solid matrix of volume Vm2 (or Vm3) (figure element 97 in FIG. 9B) and pores filled with fluid with volume Vw2 (or Vw3) (figure element 98 in FIG. 9B). Here, the index 2 refers to the time-dependent case in which the acid is still reacting with the calcite, while index 3 refers to the time when the reaction is finished and S=1. The following analysis is valid in either case.

When the acid contacts the surface of the rock, it encounters some areas with which it reacts vigorously, generating wormholes. The reaction on other parts of the rock surface is minimal, if any, and that portion is not represented in FIG. 9A. FIG. 9A can be made into a block diagram, FIG. 9B, reflecting the volume of the components described above. FIG. 9B helps to define the porosities as follows:

$$\phi_{h3} = \frac{V_{h3}}{V_t} \quad (13)$$

$$\phi_{w3} = \frac{V_{w3}}{V_t} = \left(\frac{V_{w3}}{V_{m3}+V_{w3}}\right)\left(\frac{V_{m3}+V_{w3}}{V_t}\right) = \phi_1\left(\frac{V_t-V_{h3}}{V_t}\right) \quad (13.5)$$

$$\phi_{w3} = \phi_1(1-\phi_h) \quad (14)$$

Similarly, $$\phi_{m3} = (1-\phi_1)(1-\phi_h) \quad (15)$$

It is easy to check that the sum of the terms from Equations 13, 14, and 15 add up to one, as they should. Also note that although these relations were derived for the end of acidization, and thus denoted by subscript 3, they are also valid as functions of time. These relations can be used to calculate a porosity in which the pores are filled with conductive fluid and are detectable by resistivity tool measurements (excluding the solid matrix). That is:

$$\phi_3 = \frac{V_{h3}+V_{w3}}{V_t} = \phi_{h3} + \phi_1(1-\phi_{h3}) \quad (15.5)$$

$$\phi_{h3} = \frac{\phi_3 - \phi_1}{1-\phi_1} \quad (16)$$

The term Φ1 is known from measurements before acidization, and Φ3 is determined from Equation 12. Note the same formulation applies while the acidization is in progress, in which case Equation 10 will be used to provide Φ2, which in turn leads to Φh2.

The wormhole porosity from Equation 16 is an average. It is the total porosity attributable to the wormholes in the sensitive volume Vt of the resistivity tool. If there is one wormhole and it remains entirely within Vt of this particular resistivity array, then this is the volume of that one wormhole. If more than one wormhole exists, the value from Equation 16 is the sum total volume of the individual wormholes within the volume Vt. In some embodiments the resolution of the resistivity tool may be made finer, which increases the probability of being able to map individual wormholes.

Figure 10A:
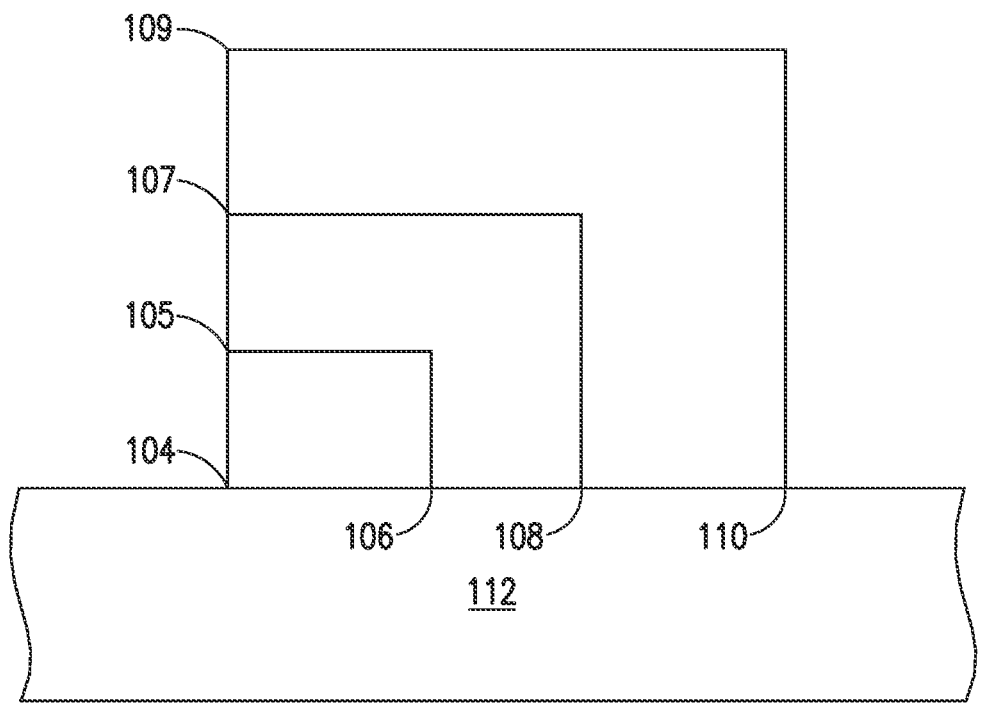
FIG. 10A is a schematic drawing showing three, overlapping sensitive regions of a three-array resistivity tool, in accordance with the present disclosure.
Figure 10B:
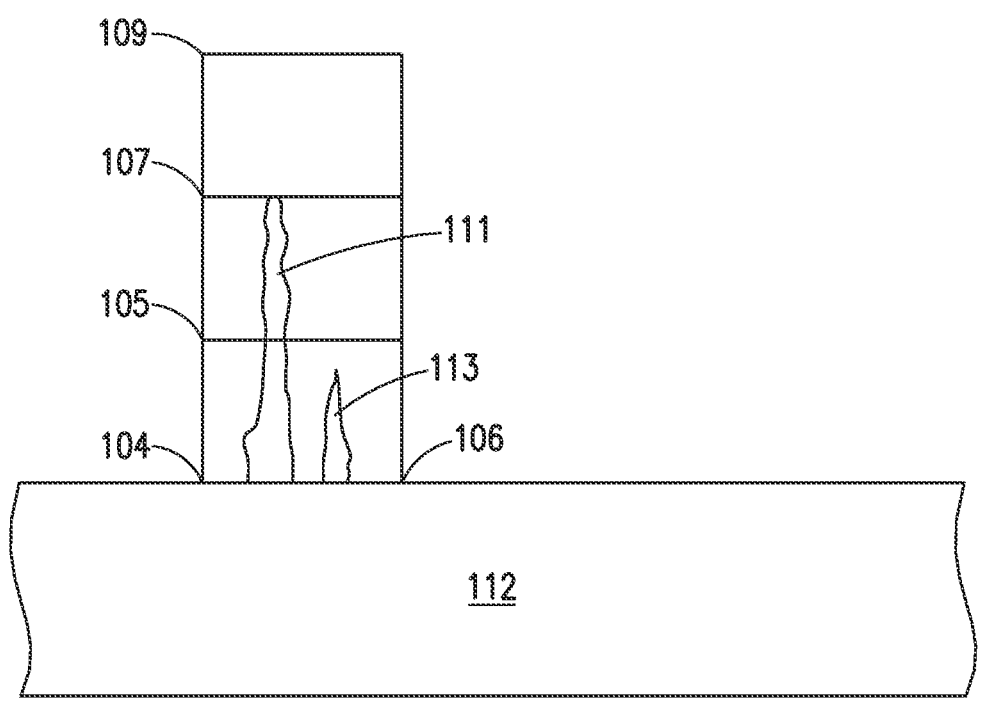
FIG. 10B is a schematic drawing showing the three sensitive regions of FIG. 10A normalized, along with two wormholes having different depths of penetration, in accordance with the present disclosure.

The radial extent of the wormhole can be determined using resistivity arrays with different depths of investigations. FIG. 10A shows the three sensitive regions of a three-array resistivity tool in which the sensitive regions happen to overlap. The array with the shallowest DOI has a sensitive region defined by 104, 105, and 106, the volume of which is Vts. Similarly, the array with medium DOI has a sensitive region defined by 104, 107, and 108, the volume of which is Vtm. The deepest DOI sensitive region is defined by 104, 109, and 110, with volume Vtd. Vts is entirely within Vtm and Vtd while Vtm has common volume with Vts but also includes a region that is not shared with Vts (105 to 107, 106 to 108). Similarly, Vtd samples the lateral extent from 106 to 110 that is not sampled by Vts in addition to the shared sample region from 104 to 106. To compare the three signals, one may divide the measured parameters by the associated lateral length of Vti (i=s, m, d). For example, for the volume bounded by 104, 107, 108, one would divide by the length scale 104 to 108. This normalization operation leads to three arrays effectively having the same lateral length but different radial extents. The resulting sensitive regions are shown in FIG. 10B. The signals from the three DOIs can now be meaningfully compared.

Resistivity tools are calibrated so that a tool's sensitivity to varying depth is calibrated out and the reported porosities from different arrays can be compared. FIG. 10B shows two wormholes 111 and 113 with different depths of penetration. In the example of FIG. 10B, when the porosities $\varnothing_{h3}$ (computed using Equation 16) determined from the different arrays are compared, the signals from the medium array and the deep array will have the same contributions from both wormholes 111 and 113 and will be equal in magnitude. That implies the wormholes do not penetrate beyond the DOI of the middle array, and therefore have a depth of penetration less than 107. The difference in signals from different arrays can be computed as:

$$\Delta\varnothing_{21} = \varnothing_3^j - \varnothing_3^i \quad (17)$$

Here the added superscripts are the resistivity array numbers. The signal from Equation 17 is equal to zero if the wormhole is entirely in the DOI of (shallower) array i, but will increase when the wormhole penetrates into the DOI of array j.

Figure 11:
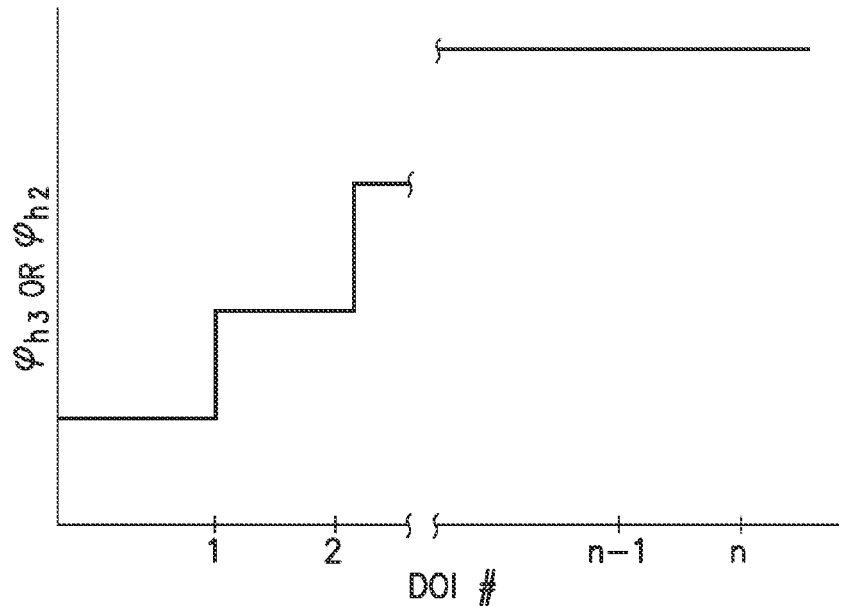
FIG. 11 is a schematic drawing showing the signal from a resistivity tool having n different arrays, and in which the signal experiences a stepwise increase as the wormhole grows, in accordance with the present disclosure.

In a further example, the signal from the shallowest array is seen to be smaller than that of the medium array, which in turn is smaller than that of the deepest array. That indicates at least some of the wormholes have penetrated beyond the depth 107. FIG. 11 shows a case where the signal from a resistivity tool ($\varnothing_{h3}$ or $\varnothing_{h2}$) having n different arrays is plotted. It shows a stepwise increase in signal as the wormhole grows. This is because a shallow wormhole is visible by the DOIs, but when the radial extent of the wormhole extends beyond the first DOI, any porosity beyond that first DOI does not contribute to the reading made by the first DOI array. In the case of FIG. 11, the signal becomes constant between the (n−1) and n arrays, suggesting no wormhole exceed the DOI of the n−1 array.

Figure 12:
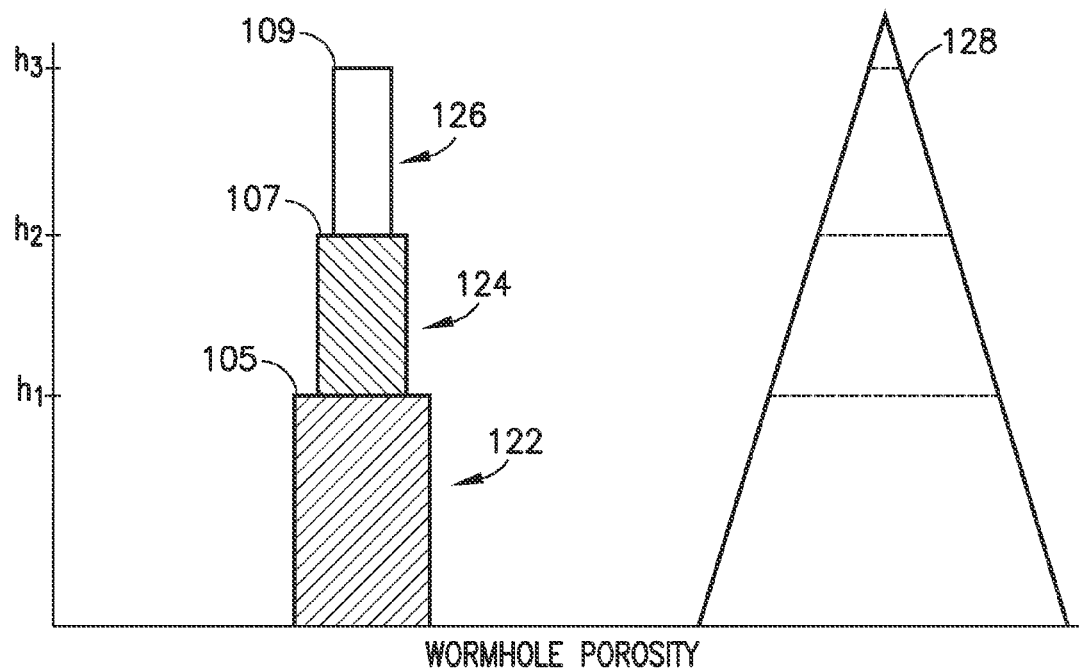
FIG. 12 is a schematic drawing showing an alternative, cone-shaped volume that may be used to approximate the shape of the aggregated wormholes, in accordance with the present disclosure.

Each of the array signals can be mapped into an effective wormhole volume for that DOI, and the three or more numbers from the three or more DOIs can be used to define a single wormhole having an average shape and volume equivalent to the wormholes, as shown in FIG. 12. In this figure, the porosities (computed using Equation 16 or 10) have been drawn as equivalent cylindrical volumes with their heights equal to their corresponding DOIs. The cross sectional area of each cylinder may be calculated using:

$$\varnothing_{3h} = 2\pi h r \quad (18)$$

Here r is the radius of an equivalent circle to the cross-sectional width of the (cylindrically represented) wormhole within the DOI of the resistivity array. To separate the contributions from different resistivity arrays, the extra porosities from Equation 17 are used (e.g., the portion of the porosity from array 2 that exceeds the porosity from the shallower array 1). The width of each one of the cylinders 122, 124, and 126 is a measure of an effective width of the wormhole.

FIG. 12 also shows an alternative, cone-shaped volume 128 that may be used to approximate the shape of the aggregated wormholes. The conical shape allows for continuous variation of the wormhole diameter. Using simple geometry, it can be shown that if the height of the cone is h, and there are three arrays with DOIs of h/3, 2h/3, and h, then the volumes of each array follow the simple ratio of 0.55:

0.89:1 for the absolute porosities (rather than the extra porosities). These numbers can be directly compared with the results from Equations 16 and 10. If in fact the ratios agree at least approximately, then the comparison indicates the wormhole has an approximately conical shape. Other shapes may be investigated and applied to the porosities derived from resistivity arrays with different DOIs to gain insight on the approximate shape of the aggregated wormholes.

Time dependence of the signals from different DOIs is another approach to gain more insight into the wormhole extent (penetration). Suppose a single wormhole is generated and is extending as a function of time. Then n arrays show a time-dependent porosity. While the wormhole is within the DOI of the first array, n arrays show the same porosities. However, once the wormhole extends beyond the DOI of the first array, the portion that is beyond the DOI of first array does not contribute to the porosity from array 1, but continues to contribute to that of the deeper arrays. This is true even if the portion of the wormhole that is in array 1 continues to widen. The increased signal from a higher DOI array compared to the first is an indication that the wormhole has grown deep enough that part of it extends beyond the DOI of the first array. Similar reasoning can be used with respect to other arrays. Using this approach the average rate of growth of the wormhole can be measured.

The resistivity tool can be moved along the length of the borehole, sampling the wormhole as a function of time. This is especially true if the rate of growth of the wormhole is slow enough that not having the tool at the same location does not corrupt the measurements. Moving the tool multiplies the number of measurements that can be made and allows more detailed information to be extracted. For example, if a section of the well is reacting at a different rate, it can be detected while the acidizing is in progress.

While the acid is reacting with the rock solid and causing the effects described above, fresh acid may be pumped into the formation. In this case any interpretation of the resistivity log should include the dynamic effect of the new acid being injected. This is an extension of the formulation described above and can be handled with properly formulated equations (usually done in the implementing software).

Attention is now directed to processing procedures, methods, techniques, and workflows that are in accordance with some embodiments. Some operations in the processing procedures, methods, techniques, and workflows disclosed herein may be combined and/or the order of some operations may be changed. Geologic interpretations, sets of assumptions, and/or domain models may be refined in an iterative fashion. This concept is applicable to the processing procedures, methods, techniques, and workflows discussed herein. This iterative refinement can include use of feedback loops executed on an algorithmic basis, such as at a computing device and/or through manual control by a user who may make determinations regarding whether a given step, action, template, or model has become sufficiently accurate.

Figure 13:
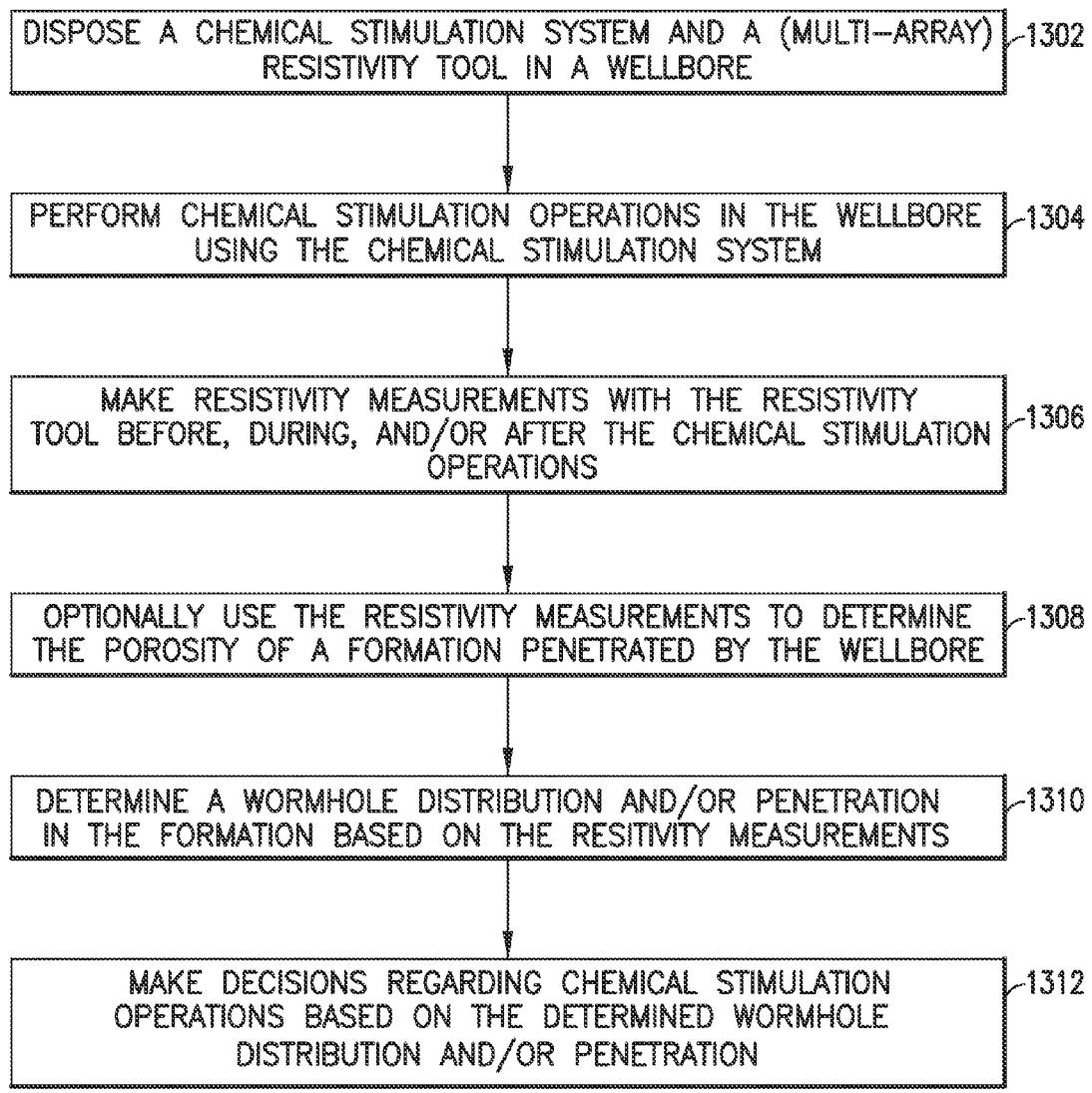
FIG. 13 is a flowchart for at least one workflow embodiment, in accordance with the present disclosure.

FIG. 13 shows a flowchart illustrating an embodiment in accordance with this disclosure. In this embodiment, the workflow comprises disposing a chemical stimulation system and a resistivity tool in a wellbore (1302); performing chemical stimulation operations in the wellbore using the chemical stimulation system (1304); making resistivity measurements with the resistivity tool before, during, and/or after the chemical stimulation operations (1306); optionally, using the resistivity measurements to determine the porosity of a formation penetrated by the wellbore (1308); determining a wormhole distribution and/or penetration in the formation based on the resistivity measurements (1310); and making decisions regarding chemical stimulation operations based on the determined wormhole distribution and/or penetration (1312).

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions, and alterations herein without departing from the scope of the present disclosure.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

While only certain embodiments have been set forth, alternatives and modifications will be apparent from the above description to those skilled in the art. These and other alternatives are considered equivalents and within the scope of this disclosure and the appended claims. Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method, comprising:
    disposing a chemical stimulation system and a resistivity tool in a wellbore;
    performing chemical stimulation operations in the wellbore using the chemical stimulation system;
    making resistivity measurements with the resistivity tool before, during, and/or after the chemical stimulation operations;
    determining a wormhole distribution and/or penetration in a formation based on the resistivity measurements ; and
    making decisions regarding stimulation operations based on the determined wormhole distribution and/or penetration.

2. The method of claim 1, wherein the chemical stimulant used by the chemical stimulation system is selected from the group consisting of: inorganic acids, organic acids, and chelating agents.

3. The method of claim 1, wherein the resistivity tool has multiple arrays.

4. The method of claim 3, wherein the multiple arrays provide measurements from multiple depths of investigation, and further comprising mapping the depths of penetration of the wormholes into the formation using the measurements from the multiple depths of investigation.

5. The method of claim 3, further comprising determining an effective wormhole volume for each depth of investigation, and, based on the effective wormhole volumes, defining a single wormhole having an average shape and volume equivalent to the effective wormhole volumes.

6. The method of claim 1, wherein the resistivity tool has one or more azimuthal arrays.

7. The method of claim 1, further comprising estimating the volume of the formation that is dissolved by the chemical stimulation operations.

8. The method of claim 1, further comprising determining a formation porosity by interpreting changes in the measured resistivities to estimate changes in the formation porosity.

9. The method of claim 1, wherein the resistivity measurements are time-dependent, and further comprising estimating the amount of spent acid using the time-dependent resistivity measurements.

10. The method of claim 1, wherein the making decisions regarding stimulation operations is done in real-time.

11. The method of claim 1, further comprising normalizing signals from two or more sensitivity regions having different depths of investigation, and determining the radial extent of one or more wormholes by comparing the normalized signals.

12. The method of claim 1, further comprising determining the conductivity of fluid flowing into the wellbore using the resistivity measurements; and determining, based on the determined fluid conductivity, one or more locations in the wellbore in which production has improved or from which unspent acid has returned into the wellbore.

13. A system, comprising:
a conveyance mechanism having a first passageway capable of receiving and delivering a chemical stimulation fluid to a desired location in a wellbore; and
a downhole resistivity tool deployed in the wellbore;
wherein measurements by the resistivity tool made prior to, during, and/or after delivery of the chemical stimulation fluid are used to infer the development of dissolution channels and the propagation of a dissolution front.

14. The system of claim 13, wherein the resistivity tool is of modular design, has a second passageway, and is integrable with the conveyance mechanism, with fluid communication between the first passageway and the second passageway.

15. The system of claim 14, wherein the modular design includes one or more spacers.

16. The system of claim 15, wherein the one or more spacers can convey the chemical stimulation fluid or allow the chemical stimulation fluid to discharge into the wellbore.

17. The system of claim 15, wherein the one or more spacers carries instrumentation.

18. The system of claim 13, wherein the resistivity tool has multiple arrays.

19. The system of claim 18, wherein the multiple arrays provide for multiple depths of investigation.

20. A system, comprising:
an integrated conveyance mechanism and resistivity tool wherein the conveyance mechanism and the resistivity tool each have fluid passageways that are in mutual fluid communication; and
wherein the integrated conveyance mechanism and resistivity tool are adapted to inject chemical stimulation fluid into a wellbore and to take resistivity measurements of a formation before, during, and/or after the injection of the chemical stimulation fluid.

21. The system of claim 20, wherein the conveyance mechanism is selected from the group consisting of coiled tubing, drill pipe, and production tubing.

22. The system of claim 20, wherein the resistivity tool is modular, each module being selected from the group consisting of a passive conduit, an instrumented conduit, and a conduit carrying one or more antennas.

* * * * *